(12) United States Patent
Hermans (10) Patent No.: US 9,290,550 B2
(45) Date of Patent: Mar. 22, 2016

(54) **COMBINATION VACCINE FOR *STREPTOCOCCUS***

(75) Inventor: Peter Wilhelmus Maria Hermans, Huissen (NL)

(73) Assignee: Stitchting Katholieke Universiteit (NL)

(*) Notice: Subject to any disclaimer, the term of this patent is extended or adjusted under 35 U.S.C. 154(b) by 0 days.

(21) Appl. No.: 13/580,728

(22) PCT Filed: Feb. 23, 2010

(86) PCT No.: PCT/NL2010/050091
§ 371 (c)(1),
(2), (4) Date: Nov. 19, 2012

(87) PCT Pub. No.: WO2011/105891
PCT Pub. Date: Sep. 1, 2011

(65) Prior Publication Data
US 2013/0071423 A1    Mar. 21, 2013

(51) Int. Cl.
*A61K 39/00*    (2006.01)
*A61K 39/02*    (2006.01)
*A61K 39/09*    (2006.01)
*A61K 39/40*    (2006.01)
*C07K 14/315*    (2006.01)

(52) U.S. Cl.
CPC ........... *C07K 14/3156* (2013.01); *A61K 39/092* (2013.01); *A61K 2039/505* (2013.01)

(58) Field of Classification Search
CPC ..... A61K 39/00; A61K 39/02; A61K 39/092; A61K 39/0208; A61K 2300/00; A61K 2309/555; A61K 35/74
See application file for complete search history.

(56) References Cited

FOREIGN PATENT DOCUMENTS

| WO | 02/077021 A2 | 10/2002 | |
|---|---|---|---|
| WO | WO 2008/127094 | * 10/2008 | ............. A61K 39/09 |
| WO | 2008/146164 A2 | 12/2008 | |

OTHER PUBLICATIONS

International Search Report issued from corresponding PCT/NL2010/050091, dated Jun. 30, 2010.
Cron, L. E., et al., "Contribution of DHH Subfamily 1 Proteins to Pneumococcal Virulence," Antonie van Leeuwenhoek, Apr. 1, 2009, pp. 43-44, vol. 95, No. 77, Springer.
Leuzzi, Rosanna, et al., "Genome Mining and Reverse Vaccinology," Handbook of Meningococcal Disease, Jan. 1, 2006, pp. 391-402, vol. 19, WILEY-VCH Verlag GmbH & Co.

* cited by examiner

*Primary Examiner* — Ja'Na Hines
(74) *Attorney, Agent, or Firm* — Banner & Witcoff, Ltd.

(57) ABSTRACT

The invention relates to the use of a combination of SP1298 and SP2205 proteins or functional fragments thereof or homologous proteins or protein fragments thereof of *S. pneumoniae* for preventing or treating a *S. pneumoniae* infection, their use for the preparation of a vaccine for the preventive treatment of a *S. pneumoniae* infection, compositions comprising said proteins of *S. pneumoniae* or functional fragments thereof, vaccines comprising said proteins or functional fragment thereof, and to a method for in vivo immune protection.

18 Claims, 6 Drawing Sheets

```
                              SP1298
  1 MEICQQILEK IKEYDTIIIH RHMKPDPDAL GSQVGLKALL EHHFPEKTIK   50
 51 AVGFDEPTLT WMAEMDLVED RAYQGALVIV CDTANTARID DKRYSQGDFL  100
101 IKIDHHPNDD VYGDLSWVDT SSSSASEMII LFAQTTQLAL ADRDAELLFA  150
151 GIVGDTGRFL YPSTTARTLR LAAYLREHNF DFAALTRKMD TMSYKIAKLQ  200
201 GYIYDHLEVD ENGAARVILS QKILKQYNIT DAETAAIVGA PGRIDRVSLW  250
251 GIFVEQADGH YRVRLRSKVH PINEIAKEHD GGGHPLASGA NSYSLEENEI  300
301 IYQKLKNLLK N
```

```
                              SP2205
  1 mkkfyvspif pilvgliafg vlstfiifvn nnlltvlilf lfvggyvflf   50
 51 KKLRVHYTRS DVEQIQYVNH QAEESLTALL EQMPVGVMKL NLSSGEVEWF  100
101 NPYAELILTK EDGDFDLEAV QTIIKASVGN PSTYAKLGEK RYAVHMDASS  150
151 GVLYFVDVSR EQAITDELVT SRPVIGIVSV DNYDDLEDET SESDISQINS  200
201 FVANFISEFS EKHMMFSRRV SMDRFYLFTD YTVLEGLMND KFSVIDAPRE  250
251 ESKQRQLPLT LSMGFSYGDG NHDEIGKVAL LNLNLAEVRG GDQVVVKEND  300
301 ETKNPVYFGG GSAASIKRTR TRTRAMMTAI SDKIRSVDQV FVVGHKNLDM  350
351 DALGSAVGMQ LFASNVIENS YALYDEEQMS PDIERAVSFI EKEGVTKLLS  400
401 VKDAMGMVTN RSLLILVDHS KTALTLSKEF YDLFTQTIVI DHHRRDQDFP  450
451 DNAVITYIES GASSASELVT ELIQFQNSKK NRLSRMQASV LMAGMMLDTK  500
501 NFTSRVTSRT FDVASYLRTR GSDSIAIQEI AATDFEEYRE VNELILQGRK  550
551 LGSDVLIAEA KDMKCYDTVV ISKAADAMLA MSGIEASFVL AKNTQGFISI  600
601 SARSRSKLNV QRIMEELGGG GHFNLAAAQI KDVTLSEAGE KLTEIVLNEM  650
651 KEKEKEE
```

```
  1  MEICQQILEK IKEYDTIIIH RHMKPDPDAL GSQVGLKALL EHHFPEKTIK   50
 51  AVGFDEPTLT WMAEMDLVED RAYQGALVIV CDTANTARID DKRYSQGDFL  100
101  IKIDHHPNDD VYGDLSWVDT SSSSASEMIT LFAQTTQLAL ADRDAELLFA  150
151  GIVGDTGRFL YPSTTARTLR LAAYLREHNF DFAALTRKMD TMSYKIAKLQ  200
201  GYIYDHLEVD ENGAARVILS QKILKQYNIT DAETAAIVGA PGRIDRVSLW  250
251  GIFVEQADGH YRVRLRSKVH PINEIAKEHD GGGHPLASGA NSYSLEENEI  300
301  IYQKLKNLLK N
```

SP2205

```
  1  mkkfyvspif pilvgliafg vlstfiifvn nnlltvlilf lfvggyvflf   50
 51  KKLRVHYTRS DVEQIQYVNH QAEESLTALL EQMPVGVMKL NLSSGEVEWF  100
101  NPYAELILTK EDGDFDLEAV QTIIKASVGN PSTYAKLGEK RYAVHMDASS  150
151  GVLYFVDVSR EQAITDELVT SRPVIGIVSV DNYDDLEDET SESDISQINS  200
201  FVANFISEFS EKHMMFSRRV SMDRFYLFTD YTVLEGLMND KFSVIDAFRE  250
251  ESKQRQLPLT LSMGFSYGDG NHDEIGKVAL LNLNLAEVRG GDQVVVKEND  300
301  ETKNPVYFGG GSAASIKRTR TRTRAMMTAI SDKIRSVDQV FVVGHKNLDM  350
351  DALGSAVGMQ LFASNVIENS YALYDEEQMS PDIERAVSFI EKEGVTKLLS  400
401  VKDAMGMVTN RSLLILVDHS KTALTLSKEF YDLFTQTIVI DHHRRDQDFP  450
451  DNAVITYIES GASSASELVT ELIQFQNSKK NRLSRMQASV LMAGMMLDTK  500
501  NFTSRVTSRT FDVASYLRTR GSDSIAIQEI AATDFEEYRE VNELILQGRK  550
551  LGSDVLIAEA KDMKCYDTVV ISKAADAMLA MSGIEASFVL AKNTQGFISI  600
601  SARSRSKLNV QRIMEELGGG GHFNLAAAQI KDVTLSEAGE KLTEIVLNEM  650
651  KEKEKEE
```

COMBINATION VACCINE FOR STREPTOCOCCUS

RELATED APPLICATION DATA

This application is a National Stage Application under 35 U.S.C. 371 of co-pending PCT application PCT/NL2010/050091 designating the United States and filed Feb. 23, 2010.

The invention relates to the field of medicine, more especially to the field of vaccines against bacterial infections, more particularly the genus *Streptococcus*, more particularly the species *Streptococcus pneumoniae*.

*Streptococcus pneumoniae* (pneumococcus, *S. pneumoniae*) is an important pathogen, which causes significant morbidity and mortality throughout the world. *S. pneumoniae* is a major cause of invasive diseases such as meningitis, bacteremia, and pneumonia, as well as non-invasive diseases like acute otitis media and sinusitis (i). In young children, the pneumococcus is often part of the normal nasopharyngeal flora. Especially during the first two years of life, children are colonised with novel strains of pneumococci. Children colonised with *S. pneumoniae* develop more often acute otitis media than children who are not colonised (ii, iii, iv).

The precise molecular mechanisms through which the pneumococcus invades and damages host tissues are not fully understood. For many years, the polysaccharide capsule has been recognised in the art as the major virulence factor and, consequently, an important vaccine candidate (for review, see v, vi). The current pneumococcal vaccine strategies focus on the use of conjugates, in which a limited number of different capsular polysaccharides are linked to a carrier protein (vii, viii). Although the results of early trials look promising, problems still arise since large-scale vaccination over time generally leads to a shift in serotype distribution towards capsular types that are poorly immunogenic or not included in the vaccine. Such a shift may be enhanced by the frequent horizontal exchange of capsular genes, as described by several investigators (ix, x, xi).

Over the last few years, much attention has been focused on the role of pneumococcal proteins in pathogenesis and protection. Proteins that are involved in the pathogenesis of infections by *S. pneumoniae* are considered to be interesting components for future conjugate vaccines. Such proteins are able to switch the immune response against the polysaccharides present in the vaccine from T-cell independent to T-cell dependent, through which the antibody response towards the polysaccharides may be increased and a memory response will be provided. In addition, such proteins should provide protection against colonisation and infection with *S. pneumoniae* strains whose capsular polysaccharides are not included in the vaccine.

The protective abilities of various (virulence) proteins have been investigated previously. Immunisation of pneumolysin (xii), pneumococcal surface protein A (PspA) (xiii, xiv, xv) pneumococcal surface adhesin A (PsaA) (xvi), and neuraminidase (xvii) clearly confer protection in animals.

In the literature various polynucleotides of *S. pneumoniae* and polypeptides predicted to be encoded by said nucleotides have been reported and the use of these compounds in vaccines and medicinal preparation has been contemplated, for instance in WO 97/37026, WO 00/06737 and WO 98/18930. These publications however, do not identify any functional protein let alone a vaccine based on a functional protein. These publications are further silent in respect of proteins that when used in vaccines are able to elicit an immuneresponse let alone that they are able to elicit any protective activity.

Currently available are a 23-valent polysaccharide vaccine (Pneumovax 23™, Merck, USA) and a 7-valent pneumococcal conjugate vaccine (Prevenar™, Wyeth, USA) giving good immune protection. However, there are limitations with these vaccines. Both polysaccharide and conjugate vaccines only protect against the vaccine type serotypes, allowing replacement of non-vaccine serotypes to occur. This serotype replacement and subsequent disease has emphasized the need for alternative vaccine strategies.

The world is in need of an effective, low-cost vaccine that would ideally provide immunologic protection against all pneumococcal serotypes, pneumococcal colonization and invasive disease. The vaccine would be immunogenic in all age groups and elicit a boostable response.

The present invention identifies a multi-component protein vaccine which encompasses several conserved pneumococcal proteins which have shown some degree of protection in murine models as novel vaccine candidates.

It has now been found that a combination of two proteins of *S. pneumoniae* can be used in the preparation of a vaccine against micro-organisms and especially *S. pneumoniae*. These proteins are amongst a large group of proteins that was detected during a genome-wide negative selection screen for bacterial factors contributing to colonization, bacteremia, and meningitis in vivo (WO 2008/127094 and PCT/NL2009/050600).

The invention accordingly relates to an immunological composition, a vaccine or medical preparation comprising the proteins SP1298 and SP2205 and/or fragments thereof and/or homologous and/or functionally homologous proteins and/or fragments thereof for the treatment of microbial infections and especially of *S. pneumoniae* infections and for the generation of antibodies in an immunised or vaccinated vertebrate host and which expresses opsonophagocytic activity against *S. pneumoniae* and infections thereof. The invention also relates to the use of these proteins or fragments thereof for the preparation of a vaccine for the treatment of a *S. pneumoniae* infection and/or colonisation and to the use of these proteins or fragments thereof or recombinant or synthetic proteins or fragments or functionally homologous proteins or fragments thereof as a carrier for inducing prophylactic protection against other micro-organisms including viruses.

In this description and the appending claims treatment encompasses and generally is the prophylaxis of infections.

The term "functional fragment" refers to a shortened version of the protein, which is a functional variant or functional derivative. A "functional variant" or a "functional derivative" of a protein is a protein the amino acid sequence of which can be derived from the amino acid sequence of the original protein by the substitution, deletion and/or addition of one or more amino acid residues in a way that, in spite of the change in the amino acid sequence, the functional variant retains at least a part of at least one of the biological activities of the original protein that is detectable for a person skilled in the art. A functional variant is generally at least 60% homologous (preferably the amino acid sequence is at least 60% identical), advantageously at least 70% homologous and even more advantageously at least 80 or 90% homologous to the protein from which it can be derived. A functional variant may also be any functional part of a protein; the function in the present case being particularly but not exclusively essential activity for nasopharyngeal colonization or infection of middle ear, lung, blood and/or meningi. "Functional" as used herein means functional in *Streptococcus pneumoniae* bacteria and capable of eliciting antibodies which give protection against disease caused by said bacteria.

The expression "conservative substitutions" as used with respect to amino acids relates to the substitution of a given amino acid by an amino acid having physicochemical characteristics in the same class. Thus where an amino acid of the SP1298 and/or SP2205 proteins has a hydrophobic characterising group, a conservative substitution replaces it by another amino acid also having a hydrophobic characterising group; other such classes are those where the characterising group is hydrophilic, cationic, anionic or contains a thiol or thioether. Such substitutions are well known to those of ordinary skill in the art, i.e. see U.S. Pat. No. 5,380,712. Conservative amino acid substitutions may be made, for example within the group of aliphatic non-polar amino acids (Gly, Ala, Pro, Ile, Leu, Val), the group of polar uncharged amino acids (Cys, Ser, Thr, Met, Asn, Gln), the group of polar charged amino acids (Asp, Glu, Lys, Arg) or the group of aromatic amino acids (His, Phe, Tyr, Trp).

The term "immunogenic part" includes reference to any part of a protein especially SP1298 and/or SP2205, or a functional homologue or functional fragment thereof, which is capable of eliciting an immune response in a mammal. Said immunogenic part preferably corresponds to an antigenic determinant of said pathogen.

As used herein, the term "antigen" refers to a molecule capable of being bound by an antibody or a T cell receptor (TCR) if presented by molecules of the major histocompatibility complex (MHC). The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a T-Helper cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. Antigens, as used herein, include infectious disease antigens, more especially antigens of *Streptococcus pneumoniae*, more preferable antigens derived from the SP1298 and/or SP2205 proteins and fragments and derivatives thereof.

As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant may contain one or more epitopes.

The term "prophylactic or therapeutic treatment of an infection by *Streptococcus pneumoniae*" or "prophylactic or therapeutic treatment of a pneumococcal infection" refers to both prophylactic or therapeutic treatments wherein virulence of the pathogen is blocked or diminished, but also to treatments wherein antibodies against the SP1298 and/or SP2205 proteins recognize the bacteria and will protect the host against infection, either directly through immune clearance, or indirectly by blocking the activity of the protein, thereby inhibiting the growth of the bacteria. Also, the term refers to blocking the function of the SP1298 and/or SP2205 proteins in vivo thereby reducing the adhesion abilities of the pathogen with a concomitant reduction in colonization and invasion capabilities. The term thus includes inducing immune responses in subjects using vaccine formulations of the invention, as well as inhibiting growth of the pathogen in vivo by using antibodies of the present invention as an active compound in a pharmaceutical composition administered to the subject. Also included is the inhibition of the virulence and/or growth of the bacteria by treatment with antibiotics.

The term "antibody" refers to molecules which are capable of binding an epitope or antigenic determinant and includes reference to antigen binding forms of antibodies (e.g., Fab, F(ab)2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies). The antibody can be monoclonal or polyclonal and can be prepared by techniques that are well known in the art such as immunization of a host and collection of sera (polyclonal) (see, e.g., Parker, Radioimmunoassay of Biologically Active Compounds, Prentice-Hall (Englewood Cliffs, N.J., U.S., 1976), Butler, *J. Immunol. Meth.* 7, 1-24 (1975); Broughton and Strong, *Clin. Chem.* 22, 726-732 (1976); and Playfair, et al., *Br. Med. Bull.* 30, 24-31 (1974)) or by preparing continuous hybrid cell lines and collecting the secreted protein (monoclonal) (see, e.g., Kohler et al in *Nature* 256, 495-497 (1975) and *Eur. J. Immunol.* 6, 511-519 (1976); by Milstein et al. *Nature* 266, 550-552 (1977); and by Walsh *Nature* 266, 495 (1977)) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others, such as CDR fragments, which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized monoclonal antibodies" means that at least a portion of the exposed amino acids in the framework regions of the antibody (or fragment), which do not match with the corresponding amino acids in the most homologous human counterparts, are changed, such as by site directed mutagenesis of the DNA encoding the antibody. Because these exposed amino acids are on the surface of the molecule, this technique is called "resurfacing." Moreover, because the amino acids on the surface of the molecule are the ones most likely to give rise to an immune response, this resurfacing decreases the immunogenicity of the monoclonal antibody when administered to a species whose cell line was not used to generate the antibody, such as a human. The term "humanized monoclonal antibody" also includes chimeric antibody wherein the light and heavy variable regions of a monoclonal antibody generated by a hybridoma from a non-human cell line are each attached, via recombinant technology, to one human light chain constant region and at least one heavy chain constant region, respectively. The preparation of such chimeric (i.e., humanized) antibodies are well known in the art.

The term "specifically recognizing", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Specific binding to an antibody under such conditions may require an antibody that is selected for its specificity for a particular protein. For example, antibodies raised to the SP1298 and/or SP2205 proteins of the present invention can be selected to obtain antibodies specifically recognizing said proteins. The proteins used as immunogens can be in native conformation or denatured so as to provide a linear epitope. A variety of immunoassay formats may be used to select antibodies specifically recognizing a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity.

A "subject" as referred to herein is meant to include mammals and other animals, wherein mammals include for example, humans, apes, monkeys, horses, cattle, pigs, goats, dogs, cats, rats, mice, and sheep. The term "non-human animal" is meant to disclaim humans. Preferably in the present invention, the subject is a human, more preferably a child or an elderly person.

Figure 1:
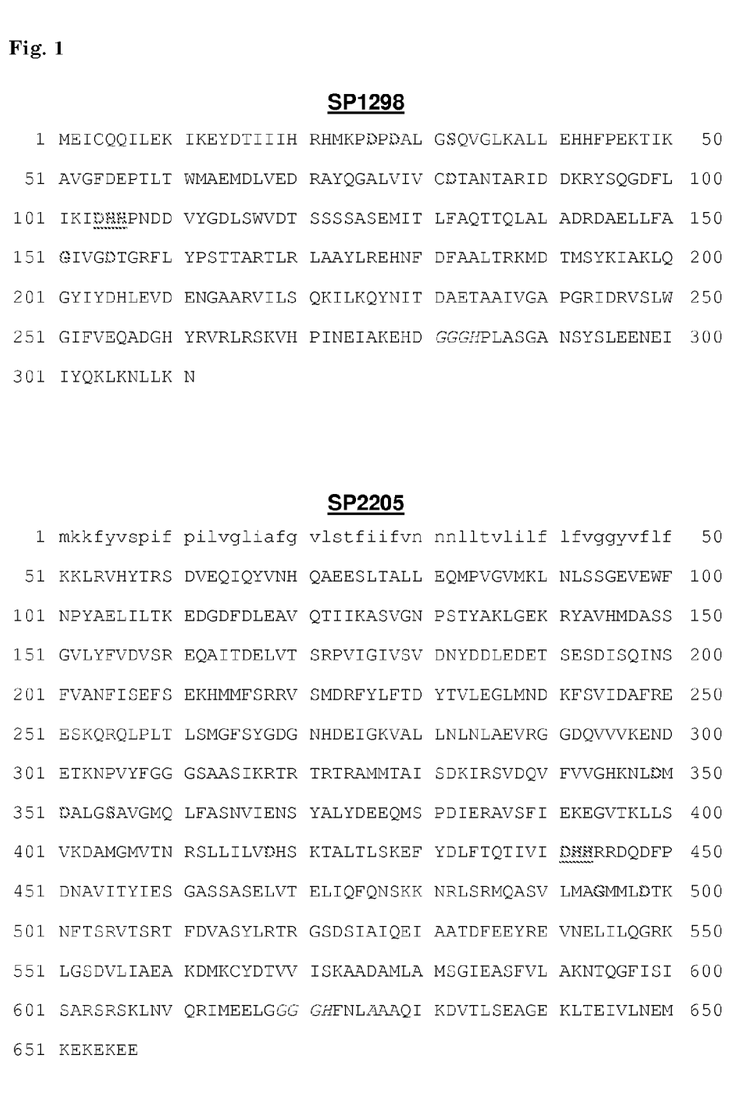
FIG. 1. Amino acid (AA) sequences of SP1298 (311 AA; top) (SEQ ID NO:1) and SP2205 (657 AA; bottom) (SEQ ID NO:2). Conservation of the DHH consensus domain (pfam01368) in both proteins is indicated by bold font, and conservation of the DHH-associated (DHHA1) consensus domain (pfam02272) by italics. The transmembrane domains (first 50 AA) removed for expression of SP2205 are indicated by small (i.e. non-capital) characters.

The proteins SP1298 and SP2205 have an amino acid sequence as provided in FIG. 1. The proteins SP1298 and SP2205 of the present invention have been identified by genomic array footprinting (GAF), which is a high-throughput method to identify conditionally essential genes in *Streptococcus pneumoniae* by using a combination of random transposon mutagenesis and microarray technology (see Bijlsma, J. J. E. et al., 2007, Appl. Environm. Microbiol. 73(5):1514-1524, and WO 2008/127094). GAF detects the transposon insertion sites in a mutant library by amplifying and labelling the chromosomal DNA adjacent to the transposon and subsequent hybridisation of these probes to a microarray. Identification of transposon insertion sites in mutants that have disappeared from the library due to selection, which represent conditionally essential genes, is achieved by differential hybridisation of the probes generated from the library grown under two conditions to an array. For the detection of essential genes for nasopharyngeal colonization and/or dissemination to and/or survival in the blood, mutant libraries of *Streptococcus pneumoniae* were used to infect mice in a murine pneumonia model of infection. For specific detection of essential genes for nasopharyngeal colonization, mutant libraries of *Streptococcus pneumoniae* were used to infect mice in a murine colonization model of infection. For specific detection of essential genes for survival in the blood, mutant libraries of *Streptococcus pneumoniae* were used to infect mice in a murine bacteraemia model of infection. After challenge mutants were identified that had disappeared from the nasopharyngeal lavage and/or blood samples taken from the mice, and the disrupted genes of these mutants were identified. SP1298 and SP2205 were amongst the proteins that have been identified as being candidates for vaccine development.

It has now surprisingly been found that a combination of both proteins is more effective in developing an immunologic response than the individual proteins.

In a preferred embodiment of the invention the protein or fragment(s) thereof used in the preparation of the vaccine, is SP1298 or a (functional) homologous fragment thereof of *S. pneumoniae*. Additionally, the vaccine may contain SP2205 or any other immunogenic protein.

In an alternative embodiment of the invention the protein or fragment(s) thereof used in the preparation of the vaccine, is SP2205 or a (functional) homologous fragment thereof of *S. pneumoniae*. Additionally, the vaccine may contain SP1298 or any other immunogenic protein.

The most preferred embodiment of the invention is where both SP1298 and SP2205 or functional fragment(s) thereof or homologous proteins or functional fragments thereof are used in the preparation of a vaccine. Additionally such a vaccine may comprise other immunogenic proteins, such as any of the proteins listed in WO 2008/127094 and PCT/NL2009/050600.

It is likewise possible to employ a fragment of SP1298 and/or SP2205 for the preparation of a vaccine. A fragment is a polypeptide with an amino acid sequence which is functionally similar to the corresponding section of the protein. A preferred fragment is an oligopeptide that contains one of the characterising parts or active domains of the protein. The proteins or the functional fragments thereof can be obtained by recombinant techniques or by chemical synthesis. Synthetic oligopeptides based on or derived from SP1298 and/or SP2205 can for instance be obtained by conventional pepscan technology. A person of skill in the art can easily prepare fragments or homologous proteins of both SP1298 and/or SP2205. Further, the applicability of these fragments or homologous proteins for providing an immunological response to *S. pneumoniae* infection can be readily tested by the skilled person by e.g. performing experiments such as described in the experimental section below.

The proteins or (functional) fragments that are used in the preparation of the vaccine can be partially purified proteins, purified proteins or fragments of SP1298 and/or SP2205.

In order to obtain a vaccine that can be administered, the protein or proteins or fragments are brought into a form that is suitable for this purpose. To this end, the protein(s) can be conjugated with a carrier protein. Carrier proteins that can be used in this invention are in general conventional carriers and as such are well known in the art. The vaccine can likewise also comprise adjuvants and other additional components to further ensure the proper functioning of the vaccine. These additional components are generally known by the skilled man.

In a preferred embodiment of the invention, the composition comprising the protein(s) or the fragment(s) are therefore combined with an adjuvant and/or a carrier. From this composition a vaccine is prepared which is used in the preventive vaccination against *S. pneumoniae*.

The invention further provides for a method for the preparation of a vaccine against *S. pneumoniae*. The method comprises the steps of preparing or isolating the protein or the fragment or homologue or functional homologue of the protein or fragment, determining the immunogenic response by raising antibodies against the protein or the fragment or homologue or functional homologue of the protein or fragment and testing the antibodies for activity. The method according to the invention also encompasses the recombinant or synthetic production of the protein or the fragment or homologue or functional homologue of the protein or fragment and the subsequent steps to the preparation of the vaccine.

The vaccine antigens of this invention are administered at a concentration that is therapeutically effective to prevent or treat infections by *Streptoccus pneumoniae*. To accomplish this goal, the vaccines may be formulated using a variety of acceptable excipients known in the art. Typically, the vaccines are administered by injection, either intravenously or intraperitoneally. Methods to accomplish this administration are known to those of ordinary skill in the art.

Preferably the vaccine contains at least 5-150 µg of antigenic mass per dose, more preferably 50-100 µg and most preferably 80 µg per dose. The antigenic mass being the mass of the antigen protein. Vaccines according to the present invention with an antigenic mass up to 275 µg per dose could even be prepared, and such vaccines may still not elicit local reactions at the injection site. Of course even more micrograms of antigen can be put in a vaccine dose of a vaccine according to the invention, but if the protection obtained with the vaccine is not improved with a higher dose the increase in antigenic load only results in the vaccine being more expensive than necessary. In addition an increasing dose of antigen may eventually lead to unacceptable local reactions at the injection site, which should be avoided.

A vaccine according to the invention may contain a (partially) purified or recombinant SP1298 and/or SP2205 protein or a functional fragment thereof, wherein said recombinant protein is preferably produced by way of expression from a expression vector in suitable host cells, said expression vector containing the gene sequence or an immunogenic part thereof under control of a suitable promoter. Several suitable expression systems are known in the art and may be used in a method to prepare a vaccine according to the invention.

A vaccine according to the invention may further comprise a suitable adjuvant. Many adjuvant systems are known in the art, for example commonly used oil in water adjuvant systems. Any suitable oil may be used, for example a mineral oil known in the art for use in adjuvants. The oil phase may also contain a suitable mixture of different oils, either mineral or non-mineral. Suitable adjuvants may also comprise vitamin E, optionally mixed with one or more oils. The water phase of an oil in water adjuvated vaccine will contain the antigenic material. Suitable formulations will usually comprise from about 25-60% oil phase (40-75% water phase). Examples of suitable formulations may comprise 30% water phase and 70% oil phase or 50% of each. Especially preferred is a non-recombinant lactococcal-based vaccine displaying the herein mentioned pneumococcal antigenic proteins or fragments thereof. The lactococcal-derived bacterial shaped particles are non-living and are designated Gram-positive Enhancer Matrix (GEM) particles (Van Roosmalen, M. L. et al., 2006, Methods 38:144-149). These GEM particles are deprived of surface proteins and the intracellular content is largely degraded (Bosma, T. et al., 2006, Appl. Environ. Microbiol. 72:880-889). The GEM particles can be used as anchoring and delivery vehicle for pneumococcal proteins (see Audouy, S. A. L. et al., 2007, Vaccine 25(13):2497).

The vaccine formulations of the present invention may be used in prophylactic methods of the invention by immunizing a subject by introducing said formulations into said subject subcutaneously, intramuscularly, intranasally, intradermally, intravenously, transdermally, transmucosally, orally, or directly into a lymph node. In another embodiment, the composition may be applied locally, near a local pathogen reservoir against which one would like to vaccinate.

The present invention further provides a method for the manufacture of a vaccine intended for the protection of a subject against pneumococcal infection, wherein said vaccine is combined with a pharmaceutically acceptable diluent, carrier, excipient or adjuvant therefore, such that a formulation is provided which can provide a dose of at least 20 µg protein in a single administration event.

A vaccine (prepared by a method) according to the invention can be used in a method to protect a subject against pneumococcal infection.

To provide adequate protection the vaccine is preferably administered in a 2 shot vaccination regimen, whereby the first shot (priming vaccination) and second shot (boosting vaccination) are given to the subject with an interval of about 3 weeks. In this way the subject will have obtained full protection against pneumococcal infection. The vaccination is very favourable for young children.

EXAMPLES

Materials and Methods
Construction of Directed Deletion Mutants.

A megaprimer PCR method was employed to replace target genes in the genome of the *S. pneumoniae* TIGR4, D39, and SME215 strains with the spectinomycin-resistance cassette of plasmid pR412T7 (Bijlsma, J. J. E. et al., 2007, Appl. Environm. Microbiol. 73(5)1514-1524). In the first step, the spectinomycin resistance cassette and the two flanking regions of the target gene were PCR-amplified using plasmid pR412T7 or chromosomal DNA isolated from one of the three pneumococcal strains as template, respectively. Flanking regions were about 500 bp in length and contained less than 150 bp of the coding sequence of the target gene. For each flanking region, the primer closest to the target gene contained an additional sequence complementary to a spectinomycin-cassette primer. In the second step, the PCR products of the two flanking regions were fused to the spectinomycin-resistance cassette by means of overlap extension PCR, leading to incorporation of the spectinomycin resistance cassette between the two flanking regions of the target gene. The resulting PCR product was transformed into the corresponding strain as follows.

First, precompetent S. pneumoniae cell stocks were prepared. Briefly, cCAT medium (10 g liter$^{-1}$ Casamino Acids (Difco), 5 g liter$^{-1}$ tryptone (Difco), 10 g liter$^{-1}$ yeast extract (Difco), 5 g liter$^{-1}$ NaCl, 16 mM $K_2PO_4$, 0.2% glucose, and 0.15 g liter$^{-1}$ glutamine) was inoculated with several colonies and grown to an optical density at 620 nm ($OD_{620}$) of 0.25-0.3. After a 30-fold dilution of the culture in CTM medium (cCAT medium supplemented with 0.2% bovine serum albumin and 1 mM $CaCl_2$), cells were grown to an $OD_{620}$ of 0.1, pelleted, resuspended in 0.1 volume of CTM-pH 7.8 (CTM adjusted to pH 7.8 with NaOH) containing 15% glycerol, and stored at −80° C. For transformation, precompetent TIGR4, D39, or SME215 cells were grown for 15 minutes at 37° C. in a 10-fold volume of CTM-pH 7.8 supplemented with 100 ng/ml CSP (CSP-1 for D39 and SME215, CSP-2 for TIGR4). After addition of DNA, cultures were incubated for 30 min at 32° C., followed by a two-hour incubation at 37° C. After overnight growth on selective plates containing 150 µg/ml spectinomycin, single transformants were picked from the plates, pooled, grown to mid-log phase in 20 ml of GM17 medium supplemented with spectinomycin, and stored at −80° C. Transformants were selected on the basis of spectinomycin-resistance and were checked by PCR for recombination at the desired location on the chromosome. In addition, a double mutant ΔSP1298ΔSP2205 was generated in each of the three pneumococcal strains. To this end, the SP1298 gene was inactivated by allelic replacement with a trimethoprim cassette as described above, and introduced into the respective ΔSP2205 strains (spectinomycin) by transformation.

Plasmid Construction and Production of his-Tagged SP1298.

The SP1298 gene of the S. pneumoniae TIGR4 strain was PCR-amplified with LCSP1298XbaIH6F and LCSP1298BamR oligonucleotide primer pairs and cloned into the pCR2.1 cloning vector of the TA cloning kit (Invitrogen) to obtain pLC1298. In the next step, the SP1298 gene was excised by XbaI and BamHI digestion and then subcloned into the expression plasmid vector pET11c (Novagen) to obtain pLC1298Xba1_#1. The nucleotide sequence of the cloned SP1298 gene was confirmed by sequencing.

For production of His-tagged SP21298, overnight cultures of E. coli BL21 (pLC1298Xba1_#1) were 50-fold diluted in prewarmed (37° C.) 2×LB supplemented with 0.5% glucose and 100 µg/ml ampicillin. At an $OD_{600}$ between 0.6 and 0.8, IPTG was added to a final concentration of 0.1 mM. After 2 hrs, cells were pelleted, resuspended in lysis buffer (20 mM sodium phosphate, 0.5 M sodium chloride, pH 7.4, and 10 mM Imidazole) to $OD_{600}$ equivalent to 100, and lysed by sonication. Insoluble debris in the lysate was removed by ultracentrifugation at 40,000 rpm for 60 min. The resulting supernatant was loaded onto a 1 ml HiTrap Chelating HP column (Amersham Biosciences) with Nickel for purification, eluted at 300 mM Imidazole and the fractions containing SP1298 were dialyzed against 10 mM Hepes. After dialysis, rHisSP1298 was freeze-dried and stored at −20° C. until further use. The identity of the purified protein was confirmed by MALDI-TOF analysis, and the concentration was determined by the bicinchoninic acid assay (Bio-Rad).

Plasmid Construction and Production of his-Tagged SP2205.

The SP2205 gene of the S. pneumoniae TIGR4 strain was PCR-amplified with LCSP2205AvrH6F and LCSP2205BamR and cloned into the pCR2.1 cloning vector of the TA cloning kit (Invitrogen) to obtain pLC2205. In the next step, the SP2205 gene was excised by BamHI and AvrII digestion and subsequently subcloned into the expression plasmid vector pET11c (Novagen) to obtain pLC2205_6. The nucleotide sequence of the cloned SP2205 gene was confirmed by sequencing.

For production of His-tagged SP2205, overnight cultures of E. coli BL21 (pLC2205_6) were 50-fold diluted in prewarmed (37° C.) 2×LB supplemented with 0.5% glucose and 100 µg/ml ampicillin. At an $OD_{600}$ between 0.6 and 0.8, IPTG was added to a final concentration of 0.1 mM. After 2 hrs, cells were pelleted, resuspended in lysis buffer (20 mM sodium phosphate, 0.5 M sodium chloride, pH 7.4, 10 mM Imidazole, 6M urea, 1 mM PMSF, and 10% Triton-X-100) to $OD_{600}$ equivalent to 100. Before sonication, 100 mM PMSF, 100 mM BZA, and lysozyme was added to the SP2205 pellet to improve lysis. Any additional insoluble debris in the lysate was removed by ultracentrifugation at 40,000 rpm for 60 min. The resulting supernatant was loaded onto a 1 ml HiTrap Chelating HP column (Amersham Biosciences) with Nickel for purification and eluted with 300 mM Imidazole. Fractions containing SP2205 were dialyzed against 10 mM Hepes, 6M urea, and 0.1% Triton-X 100. After dialysis, rHisSP2205 was stored in solution at −20° C. until further use. The identity of the purified protein was confirmed by MALDI-TOF analysis and the concentration was determined by the bicinchoninic acid assay (Bio-Rad).

Cell Line and Cell Culture.

The human pharyngeal epithelial cell line Detroit 562 (ATCC number CCL-138) was routinely grown in RPMI 1640 medium without phenol red (Invitrogen, The Netherlands) supplemented with 1 mM sodium pyruvate and 10% (v/v) fetal calf serum (FCS). All cells were cultured at 37° C. in a 5% $CO_2$ environment.

Adherence Assay.

For adherence assays, bacteria were grown to mid-exponential phase in THY and stored in 1-ml aliquots at −80° C. in THY containing 15% glycerol. Before each assay, bacteria were resuspended in RPMI 1640 medium without phenol red supplemented with 1% FCS. Adherence of pneumococci to epithelial cells was performed as described previously (Bootsma H. J. et al., 2007, Infect. Immun. 75:5489-5499; Hermans P. W. M. et al., 2006, J. Biol. Chem. 281(2)968-976). Briefly, Detroit 562 cells were seeded into 24-well plates and incubated for 48 h. Confluent monolayers were washed twice with PBS and infected with 1×10$^7$ CFU ml$^{-1}$ (multiplicity of infection (MOI) of 10 (bacteria/cells)) and pneumococci were allowed to adhere to the cells for 2 h at 37° C. in a 5% $CO_2$ environment. Non-adherent bacteria were removed by three 1-ml washes with PBS, after which 200 µl of 25% trypsin, 1 mM EDTA was added to detach the cells, followed by 800 µl of ice-cold 0.025% Triton X-100 in PBS to lyse the cells. Samples were plated for CFU count, and corrected to account for small differences in the initial inoculum count. All experiments were performed in triplicate and repeated at least three times. The adherence of the mutants is given as the percentage relative to the wild-type. Wild-type and mutant strains grew comparably in RPMI medium (without phenol red supplemented with 1% FCS) alone.

In Vivo Virulence Studies.

Eight-week old female outbred CD-1 mice (Charles River Laboratories) were used for all infection models. Aliquots of bacteria stored at −80° C. were rapidly thawed, harvested by centrifugation, and resuspended in sterile PBS to give the required amount of CFU/ml. Prior to infection, strains were passaged in mice to maintain virulence as described previously (Hendriksen W. T. et al., 2007, J. Bacteriol. 189:1382-1389). For the pneumonia model, mice were lightly anesthetized with 2.5% (vol/vol) isoflurane/$O_2$, and infected intranasally by pipetting 50 µl of inoculum ($5 \times 10^6$ CFU total) onto the nostrils of mice held in an upright position. At predetermined times after infection, groups of mice were sacrificed by injection anesthesia, and blood samples were removed by retro-orbital bleeding. Bacteria were recovered from the nasopharynx by flushing the nostrils with 2 ml sterile PBS (nasopharyngeal lavage, NPL). Bronchoalveolar lung lavage (BAL) was performed by flushing the lungs with 2 ml sterile PBS, after which lungs were removed from the body and homogenized in 2 ml of sterile PBS using a hand held homogenizer. In the colonization model, mice were infected intranasally with 10 µl of inoculum ($5 \times 10^6$ CFU total), a volume small enough to only infect the nose (nasopharynx) of the mice. At predetermined time-points after infection, NPL and lung were collected as described above. In the bacteremia model, mice were infected in a tail vein with a 100-µl inoculum ($10^6$-$10^7$ CFU total). Bacteria were recovered from the blood by a lateral tail vein puncture from the same mouse at 0, 12, 24 and 36 hours post-infection. The number of viable bacteria in NPL, BAL, blood and homogenized lungs was determined by plating serial 10-fold dilutions on blood agar (BA) plates.

For all co-infection experiments, a 1:1 ratio of wild-type and mutant was used to infect the mice as described in the above mentioned models. This set-up reduces variation between individual mice, inoculation preparation and distribution, and sample collection. Viable bacteria were quantified by plating serial dilutions on BA plates and BA plates supplemented with either spectinomycin or spectinomycin and trimethoprim. Subsequently, competitive index (CI) scores were calculated for each individual animal as the output ratio of mutant to wild type divided by the input ratio of mutant to wild type bacteria. For all experiments in which no mutant bacteria were recovered from a particular mouse, the number 20 (lower limit of detection) was substituted as the numerator. A log CI score of 0 indicates equal numbers of wild-type and mutant bacteria, a CI score<0 indicates that the mutant is outcompeted by the wild-type. All animal experiments were performed with approval of the Radboud University Nijmegen Medical Centre Committee for Animal Ethics.

Vaccination Study.

Female CD-1 mice (6 weeks old) were subcutaneously immunized with 150 µl of vaccine or control (alum was used as the negative control and Prevenar as the positive). Aluminum hydroxide gel (Sigma) was the adjuvant used and was formulated with each of the vaccines at 3 mg/ml. Complete immunizations consisted of three doses at 14-day intervals. Each group consisted of 10 mice. Singly vaccinated mice were given 50 µg of antigen and the mice receiving a combination of both DHH proteins received 25 µg of each. Mice were challenged with the TIGR4WT strain two and a half weeks after the last immunization in our pneumonia model and sampled 48 hours post-infection.

Detection of Antigen-Specific IgG by ELISA.

To determine the concentrations of antibodies against SP1298, SP2205, SP1298/SP2205, an ELISA procedure was used. High binding capacity microtitre plates (Greiner, Alphen aan de Rijn, The Netherlands) were coated with 1 µg/µl purified rHisSP1298 or rHisSP2205 in 100 µl/well overnight at 4° C. Plates were washed with PBS (pH 7.4) with 0.05% Tween 20, then incubated 1 h with 2% BSA in PBS/Tween. Three-fold dilutions of sera were added to the plates and incubated for 1 h at 37° C. After washing, the alkaline phosphatase secondary antibody directed to mouse IgG-Fc (Sigma-Aldrich) was incubated for 1 h at 37° C. using a 1:25000 dilution. After washing with 0.05% Tween 20, 100 µl/well of p-nitrophenyl phosphate in substrate buffer (10 mM diethanolamine and 0.5 mM magnesium chloride, pH 9.5) was added and read at 405 nm.

Statistical Analyses.

Comparisons of bacterial loads between wild-type and mutant bacterial strains were performed using Student's t-test (unpaired) for in vitro adherence and with the single mouse infection models. For the co-infection, comparison of log CI scores was performed using the one-sample t-test (with an arbitrary median of 0) with P<0.05 considered statistically significant. All statistical analyses were performed using GraphPad Prism version 4.0.

Results

Figure 2:
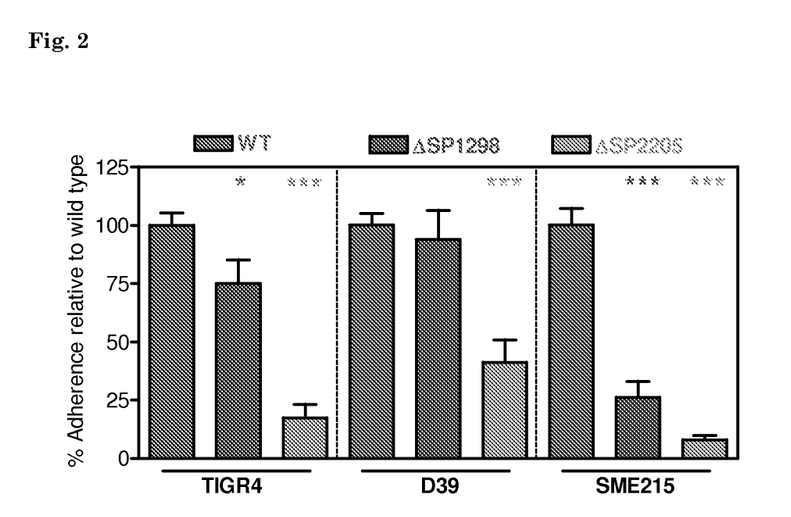
FIG. 2: Contribution of the proteins to adherence to human pharyngeal epithelial Detroit 562 cells. Left bar: wild type *S. pneumoniae*, middle bar SP1298 mutant and right bar SP2205 mutant. Adherence is expressed relative to wild-type, and the different strain backgrounds used are indicated below the x-axis.

From FIG. 2 it appears that adherence to pharyngeal epithelial cells was impaired in the SP1298 and in the SP2205 mutants when compared to their respective wild types (either TIGR4, D39 or SME215). Deletion of SP2205 showed the most dramatic effect in all three backgrounds, all being highly significant. The SP1298 mutant showed a significant decrease in adherence in the SME215 background, and a trend towards decrease in the other two strains.

Figure 3:
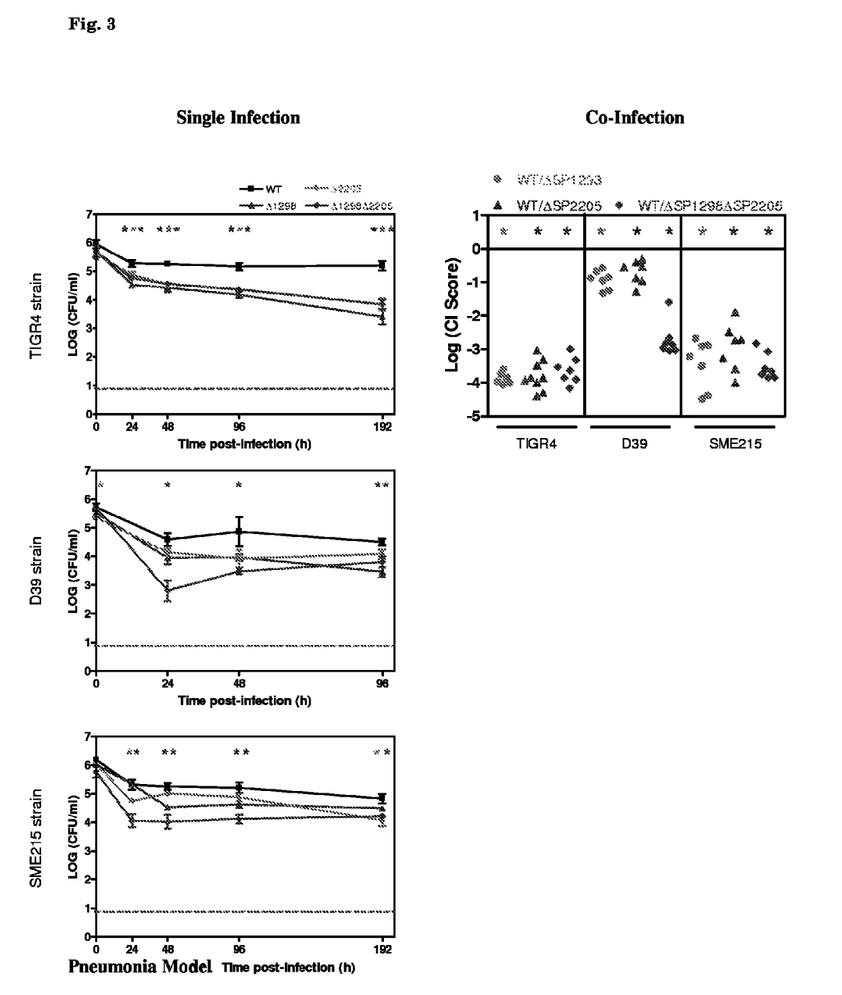
FIG. 3: Bacterial load in colonization model single infection and co-infection experiments in mice.
Figure 4:
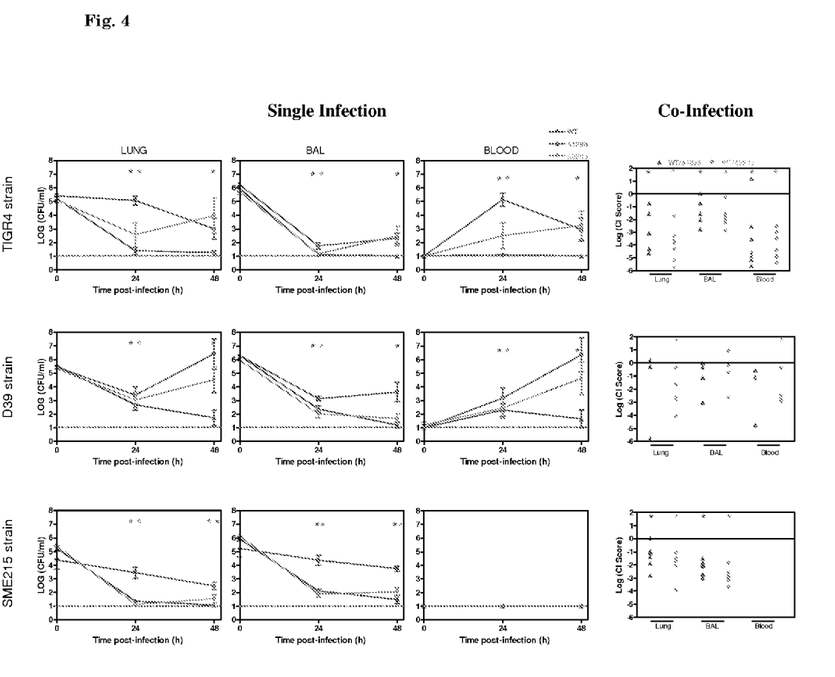
FIG. 4: Bacterial load in pneumonia model single infection and co-infection experiments in mice. Concentration in lung tissue, lung lavage (BAL) and blood.
Figure 5:
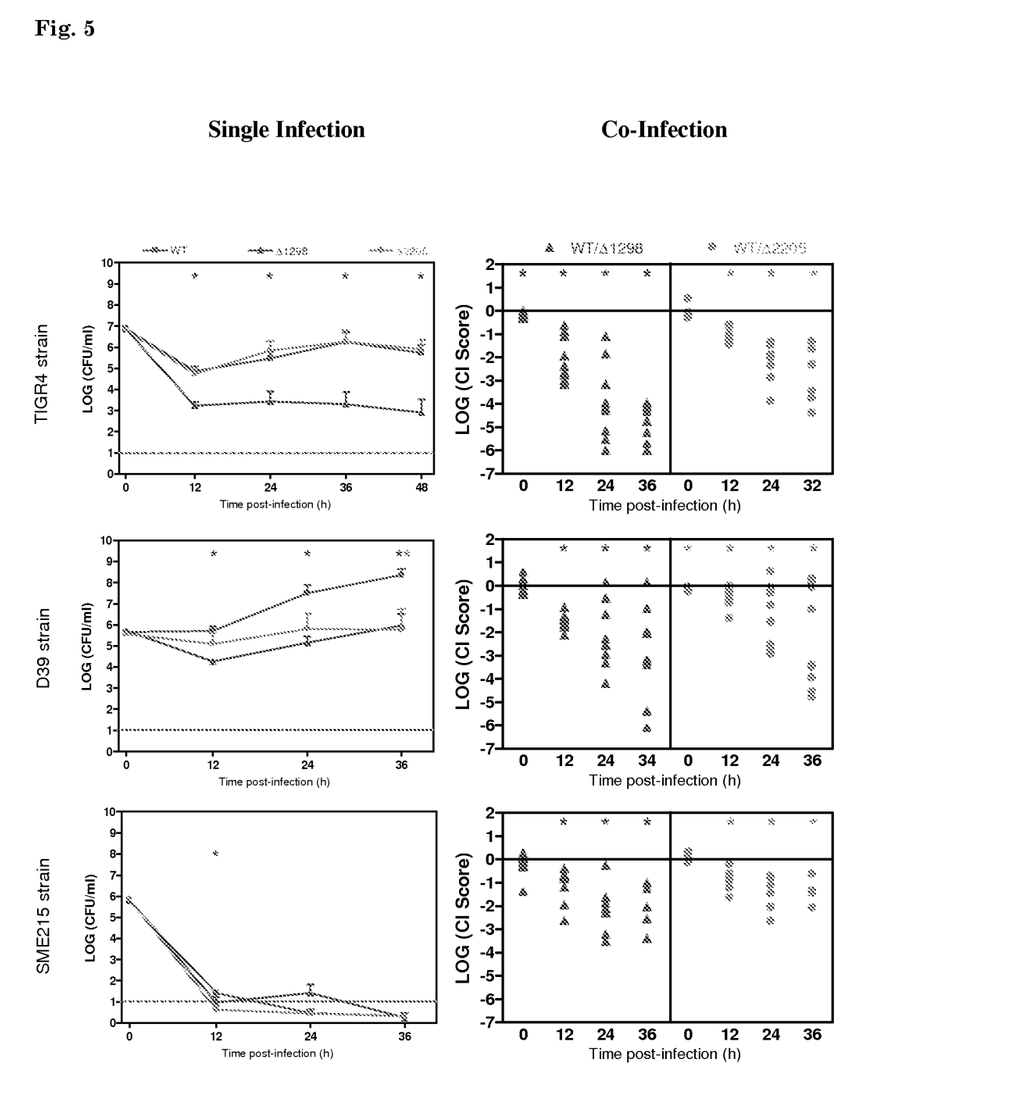
FIG. 5: Bacterial load in bacteremia model single infection and co-infection experiments in mice.
Figure 6:
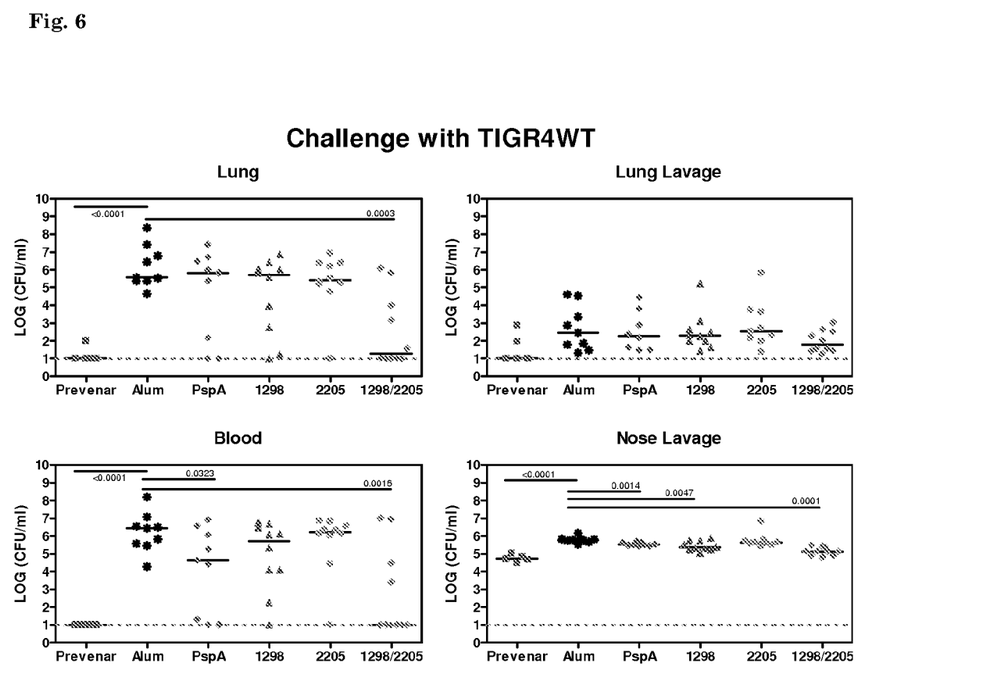
FIG. 6: Bacterial load after vaccination with one or both recombinant proteins compared with positive controls Prevenar™ and PspA and with negative control (alum) after challenge with TIGR4 wild-type.

With respect to the infection studies, in the colonization model, a significant reduction in bacterial load in both single and co-infection setup was observed for both single mutants and the double mutant (FIG. 3), especially in the TIGR4 background. No synergistic or additive effect was observed when comparing the single mutants with the double mutant, except for the D39 background, where the double mutant was considerably more outcompeted than the two single mutants. In the pneumonia model (see FIG. 4) all mutants were significantly attenuated in the lungs in all three strains, both singly and in competition with their respective wild types. In the bacteremia infection model (FIG. 5) the SP2205 mutant in TIGR4 and D39 was only attenuated in blood in a co-infection setup, suggesting that this mutant is only able to efficiently survive during bacteremia when it is not in competition with wild type. The SP1298 mutant was significantly attenuated in blood of TIGR4 and D39 during both single and co-infection.

In the vaccination study, mice were injected with either one or both recombinant proteins. As is evident from FIG. 5, only a combination of both proteins provided protection against subsequent challenge with S. pneumoniae strain TIGR4, as bacterial loads were significantly lower in the lungs and blood of these mice compared to the negative control group that received adjuvant (alum) only. As compared to the positive control (the commercially obtainable vaccine Prevenar™) the combination performed nearly as well, while the individual results of the two proteins were less pronounced or absent.

It is thus submitted that the combination of SP2205 and SP1298 is a promising vaccine composition, which confers significant protection against pneumococcal pneumonia, also indicating that both SP1298 and SP2205 could be considered as potential candidates for a multi-component protein vaccine.

REFERENCES

1. Caputo, G. M., M. Singer, S. White, and M. R. Weitekamp. 1993. Infections due to antibiotic-resistant gram-positive cocci. J. Gen. Intern. Med. 8:626-634.
2. Faden, H., L. Duffy, R. Wasielewski, J. Wolf, D. Krystofik, and Y. Tung. 1997. Relationship between nasopharyngeal colonisation and the development of otitis media in children; Tonawanda/Williamsville Pediatrics. J Infect Dis. 175:1440-1445.
3. Homoe, P., J. Prag, S. Farholt, J. Henrichsen, A. Hornsleth, M. Kilian, and J. S. Jensen. 1996. High rate of nasopharyngeal carriage of potential pathogens among children in Greenland: results of a clinical survey of middle-ear disease. Clin Infect Dis. 23:1081-1090.
4. Zenni, M. K., S. H. Cheatham, J. M. Thompson, G. W. Reed, A. B. Batson, P. S. Palmer, K. L. Holland, and K. M. Edwards. 1995. S. pneumoniae colonisation in the young child: association with otitis media and resistance to penicillin. J Pediatr. 127:533-537.
5. Alonso Develasco E, Verheul A F, Verhoef J, Snippe H. S. pneumoniae: virulence factors, pathogenesis, and vaccines. Microbiol Rev 1995; 59:591-603.
6. Mitchell T J, Alexander J E, Morgan P J, Andrew P W. Molecular analysis of virulence factors of S. pneumoniae. Soc. Appl. Bacteriol. Symp. Ser. 1997; 26:62S-71S.
7. Butler J C. Epidemiology of pneumococcal serotypes and conjugate vaccine formulations. Microb. Drug Resist. 1997; 3:125-129.
8. Dagan R, Melamed R, Muallem M, Piglansky L, Yagupsky P. Nasopharyngeal colonisation in southern Israel with antibiotic-resistant pneumococci during the first 2 years of life: relation to serotypes likely to be included in pneumococcal conjugate vaccines. J. Infect. Dis. 1996; 174:1352-1355.
9. Barnes D M, Whittier S, Gilligan P H, Soares S, Tomasz A, Henderson F W. Transmission of multidrug-resistant serotype 23F S. pneumoniae in group day care: evidence suggesting capsular transformation of the resistant strain in vivo. J. Infect. Dis. 1995; 171:890-896.
10. Hermans P W, Sluijter M, Dejsirilert S, et al. Molecular epidemiology of drug-resistant pneumococci: toward an international approach. Microb. Drug Resist. 1997; 3:243-51.
11. Hermans P W, Sluijter M, Elzenaar K, et al. Penicillin-resistant S. pneumoniae in the Netherlands: results of a 1-year molecular epidemiologic survey. J. Infect. Dis. 1997; 175:1413-22.
12. Paton J C, Lock R A, Hansman D J. Effect of immunisation with pneumolysin on survival time of mice challenged with S. pneumoniae. Infect. Immun. 1983; 40:548-52.
13. McDaniel L S, Sheffield J S, Delucchi P, Briles D E. PspA, a surface protein of S. pneumoniae, is capable of eliciting protection against pneumococci of more than one capsular type. Infect. Immun. 1991; 59:222-8.
14. Talkington D F, Crimmins D L, Voellinger D C, Yother J, Briles D E. A 43-kilodalton pneumococcal surface protein, PspA: isolation, protective abilities, and structural analysis of the amino-terminal sequence. Infect. Immun. 1991; 59:1285-9.
15. Wu M H N, Y. Guo, Michael W. Russel, and David E. Briles. Intranasal immunisation of mice with pspA (pneumococcal surface protein A) can prevent intranasal carriage, pulmonary infection, and sepsis with S. pneumoniae. J. Infect. Dis. 1997; 175:839-846.
16. Talkington D F, Brown B G, Tharpe J A, Koenig A, Russell H. Protection of mice against fatal pneumococcal challenge by immunisation with pneumococcal surface adhesin A (PsaA). Microb. Pathog. 1996; 21:17-22.
17. Lock R A, Paton J C, Hansman D. Comparative efficacy of pneumococcal neuraminidase and pneumolysin as immunogens protective against S. pneumoniae. Microb. Pathog. 1988; 5:461-7.14.

The invention claimed is:

1. A method for immunizing a subject or for therapeutic treatment of a *Streptococcus pneumoniae* infection in a subject in need of such treatment comprising administering to the subject an effective amount of a composition comprising an immunogenic combination of protein SP1298 and protein SP2205 of *Streptococcus pneumoniae*, or an immunogenic fragment(s) thereof immunogenic to *Streptococcus pneumonia*, wherein the immunogenic combination is an active ingredient in the composition and is present in an immunogenically effective amount.

2. A The method according to claim 1 wherein the composition includes at least one of a pharmaceutically acceptable diluent, carrier, excipient or adjuvant.

3. A method for administration of an immunogenic composition in a mammalian subject comprising administering to a mammalian subject an immunologically effective amount of the composition comprising an immunogenic combination of protein SP1298 and protein SP2205 of *Streptococcus pneumoniae*, or an immunogenic fragment(s) thereof immunogenic to *Streptococcus pneumonia*, wherein the immunogenic combination is an active ingredient in the composition and is present in an immunogenically effective amount.

4. The method according to claim 3, wherein the mammalian subject is a human child.

5. The method according to claim 3, wherein the composition is administered in a two shot regimen.

6. The method according to claim 5, whereby the first shot and the second shot are given to the mammalian subject in an interval of about three weeks.

7. The method according to claim 3 wherein the composition includes a pharmaceutically acceptable carrier, diluent, excipient or adjuvant.

8. The method according to claim 1, wherein the composition is immunogenic to *Streptococcus pneumonia* causing pneumonia, meningitis, otitis media or sepsis.

9. A method for therapeutic treatment of a *Streptococcus pneumoniae* infection in a subject comprising administering to a subject in need of such treatment an effective amount of a composition comprising an immunogenic combination of isolated protein SP1298 and protein SP2205 of *Streptococcus pneumoniae*, or an immunogenic fragment(s) thereof immunogenic to *Streptococcus pneumoniae*.

10. A The method according to claim 9 wherein the composition includes at least one of a pharmaceutically acceptable diluent, carrier, excipient or adjuvant, wherein at least one of SP1298 and SP2205 is recombinant.

11. A method of creating an immune response in a mammalian subject comprising administering to a subject an immunologically effective amount of the a composition comprising an immunogenic combination of isolated protein SP1298 and protein SP2205 of *Streptococcus pneumoniae*, or an immunogenic fragment(s) thereof immunogenic to *Streptococcus pneumoniae* which creates an immune response in the presence of *Streptococcus pneumoniae*.

12. The method according to claim 11, wherein the mammalian subject is a human child.

13. The method according to claim 11, wherein the composition is administered in a two shot regimen.

14. The method according to claim 13, whereby the first shot and the second shot are given to the mammalian subject in an interval of about three weeks.

15. The method according to claim 11 wherein the composition further includes at least one of a pharmaceutically acceptable diluent, carrier, excipient or adjuvant.

16. The method according to claim 1 wherein at least one of protein SP1298 and protein SP 2205 is recombinant.

17. The method according to claim 11 wherein at least one of protein SP1298 and protein SP 2205 is recombinant.

18. The method according to claim 1 wherein the composition includes 5-150 µg of the immunogenic combination of protein SP1298 and protein SP2205 per dose.

\* \* \* \* \*

SEQUENCE LISTING

```
<160> NUMBER OF SEQ ID NOS: 2

<210> SEQ ID NO 1
<211> LENGTH: 311
<212> TYPE: PRT
<213> ORGANISM: Streptococcus pneumoniae

<400> SEQUENCE: 1

Met Glu Ile Cys Gln Gln Ile Leu Glu Lys Ile Lys Glu Tyr Asp Thr
1               5                   10                  15

Ile Ile Ile His Arg His Met Lys Pro Asp Pro Asp Ala Leu Gly Ser
            20                  25                  30

Gln Val Gly Leu Lys Ala Leu Leu Glu His His Phe Pro Glu Lys Thr
        35                  40                  45

Ile Lys Ala Val Gly Phe Asp Glu Pro Thr Leu Thr Trp Met Ala Glu
    50                  55                  60

Met Asp Leu Val Glu Asp Arg Ala Tyr Gln Gly Ala Leu Val Ile Val
65                  70                  75                  80

Cys Asp Thr Ala Asn Thr Ala Arg Ile Asp Asp Lys Arg Tyr Ser Gln
                85                  90                  95
```

-continued

Gly Asp Phe Leu Ile Lys Ile Asp His His Pro Asn Asp Val Tyr
              100                 105                 110

Gly Asp Leu Ser Trp Val Asp Thr Ser Ser Ser Ala Ser Glu Met
              115                 120                 125

Ile Thr Leu Phe Ala Gln Thr Thr Gln Leu Ala Leu Ala Asp Arg Asp
130                 135                 140

Ala Glu Leu Leu Phe Ala Gly Ile Val Gly Asp Thr Gly Arg Phe Leu
145                 150                 155                 160

Tyr Pro Ser Thr Thr Ala Arg Thr Leu Arg Leu Ala Ala Tyr Leu Arg
              165                 170                 175

Glu His Asn Phe Asp Phe Ala Ala Leu Thr Arg Lys Met Asp Thr Met
              180                 185                 190

Ser Tyr Lys Ile Ala Lys Leu Gln Gly Tyr Ile Tyr Asp His Leu Glu
              195                 200                 205

Val Asp Glu Asn Gly Ala Ala Arg Val Ile Leu Ser Gln Lys Ile Leu
              210                 215                 220

Lys Gln Tyr Asn Ile Thr Asp Ala Glu Thr Ala Ala Ile Val Gly Ala
225                 230                 235                 240

Pro Gly Arg Ile Asp Arg Val Ser Leu Trp Gly Ile Phe Val Glu Gln
              245                 250                 255

Ala Asp Gly His Tyr Arg Val Arg Leu Arg Ser Lys Val His Pro Ile
              260                 265                 270

Asn Glu Ile Ala Lys Glu His Asp Gly Gly His Pro Leu Ala Ser
              275                 280                 285

Gly Ala Asn Ser Tyr Ser Leu Glu Glu Asn Glu Ile Ile Tyr Gln Lys
              290                 295                 300

Leu Lys Asn Leu Leu Lys Asn
305                 310

<210> SEQ ID NO 2
<211> LENGTH: 657
<212> TYPE: PRT
<213> ORGANISM: Streptococcus pneumoniae

<400> SEQUENCE: 2

Met Lys Lys Phe Tyr Val Ser Pro Ile Phe Pro Ile Leu Val Gly Leu
1               5                   10                  15

Ile Ala Phe Gly Val Leu Ser Thr Phe Ile Ile Phe Val Asn Asn Asn
              20                  25                  30

Leu Leu Thr Val Leu Ile Leu Phe Leu Phe Val Gly Gly Tyr Val Phe
              35                  40                  45

Leu Phe Lys Lys Leu Arg Val His Tyr Thr Arg Ser Asp Val Glu Gln
50                  55                  60

Ile Gln Tyr Val Asn His Gln Ala Glu Glu Ser Leu Thr Ala Leu Leu
65                  70                  75                  80

Glu Gln Met Pro Val Gly Val Met Lys Leu Asn Leu Ser Ser Gly Glu
              85                  90                  95

Val Glu Trp Phe Asn Pro Tyr Ala Glu Leu Ile Leu Thr Lys Glu Asp
              100                 105                 110

Gly Asp Phe Asp Leu Glu Ala Val Gln Thr Ile Ile Lys Ala Ser Val
              115                 120                 125

Gly Asn Pro Ser Thr Tyr Ala Lys Leu Gly Glu Lys Arg Tyr Ala Val
              130                 135                 140

His Met Asp Ala Ser Ser Gly Val Leu Tyr Phe Val Asp Val Ser Arg
145                 150                 155                 160

-continued

```
Glu Gln Ala Ile Thr Asp Glu Leu Val Thr Ser Arg Pro Val Ile Gly
            165                 170                 175
Ile Val Ser Val Asp Asn Tyr Asp Leu Glu Asp Thr Ser Glu
        180                 185                 190
Ser Asp Ile Ser Gln Ile Asn Ser Phe Val Ala Asn Phe Ile Ser Glu
            195                 200                 205
Phe Ser Glu Lys His Met Met Phe Ser Arg Arg Val Ser Met Asp Arg
210                 215                 220
Phe Tyr Leu Phe Thr Asp Tyr Thr Val Leu Glu Gly Leu Met Asn Asp
225                 230                 235                 240
Lys Phe Ser Val Ile Asp Ala Phe Arg Glu Glu Ser Lys Gln Arg Gln
            245                 250                 255
Leu Pro Leu Thr Leu Ser Met Gly Phe Ser Tyr Gly Asp Gly Asn His
            260                 265                 270
Asp Glu Ile Gly Lys Val Ala Leu Leu Asn Leu Asn Leu Ala Glu Val
            275                 280                 285
Arg Gly Gly Asp Gln Val Val Lys Glu Asn Asp Glu Thr Lys Asn
        290                 295                 300
Pro Val Tyr Phe Gly Gly Ser Ala Ala Ser Ile Lys Arg Thr Arg
305                 310                 315                 320
Thr Arg Thr Arg Ala Met Met Thr Ala Ile Ser Asp Lys Ile Arg Ser
            325                 330                 335
Val Asp Gln Val Phe Val Val Gly His Lys Asn Leu Asp Met Asp Ala
            340                 345                 350
Leu Gly Ser Ala Val Gly Met Gln Leu Phe Ala Ser Asn Val Ile Glu
            355                 360                 365
Asn Ser Tyr Ala Leu Tyr Asp Glu Glu Gln Met Ser Pro Asp Ile Glu
        370                 375                 380
Arg Ala Val Ser Phe Ile Glu Lys Glu Gly Val Thr Lys Leu Leu Ser
385                 390                 395                 400
Val Lys Asp Ala Met Gly Met Val Thr Asn Arg Ser Leu Leu Ile Leu
            405                 410                 415
Val Asp His Ser Lys Thr Ala Leu Thr Leu Ser Lys Glu Phe Tyr Asp
            420                 425                 430
Leu Phe Thr Gln Thr Ile Val Ile Asp His His Arg Arg Asp Gln Asp
            435                 440                 445
Phe Pro Asp Asn Ala Val Ile Thr Tyr Ile Glu Ser Gly Ala Ser Ser
        450                 455                 460
Ala Ser Glu Leu Val Thr Glu Leu Ile Gln Phe Gln Asn Ser Lys Lys
465                 470                 475                 480
Asn Arg Leu Ser Arg Met Gln Ala Ser Val Leu Met Ala Gly Met Met
            485                 490                 495
Leu Asp Thr Lys Asn Phe Thr Ser Arg Val Thr Ser Thr Phe Asp
            500                 505                 510
Val Ala Ser Tyr Leu Arg Thr Arg Gly Ser Asp Ser Ile Ala Ile Gln
            515                 520                 525
Glu Ile Ala Ala Thr Asp Phe Glu Glu Tyr Arg Glu Val Asn Glu Leu
        530                 535                 540
Ile Leu Gln Gly Arg Lys Leu Gly Ser Asp Val Leu Ile Ala Glu Ala
545                 550                 555                 560
Lys Asp Met Lys Cys Tyr Asp Thr Val Val Ile Ser Lys Ala Ala Asp
            565                 570                 575
```

-continued

```
Ala Met Leu Ala Met Ser Gly Ile Glu Ala Ser Phe Val Leu Ala Lys
        580             585             590

Asn Thr Gln Gly Phe Ile Ser Ile Ser Ala Arg Ser Arg Ser Lys Leu
        595             600             605

Asn Val Gln Arg Ile Met Glu Glu Leu Gly Gly Gly Gly His Phe Asn
        610             615             620

Leu Ala Ala Ala Gln Ile Lys Asp Val Thr Leu Ser Glu Ala Gly Glu
625             630             635             640

Lys Leu Thr Glu Ile Val Leu Asn Glu Met Lys Glu Lys Glu Lys Glu
                645             650             655

Glu
```